United States Patent [19]
Hollenberg

[11] Patent Number: 5,126,382
[45] Date of Patent: Jun. 30, 1992

[54] SUPERABSORBENT COMPOSITIONS AND A PROCESS FOR PREPARING THEM

[75] Inventor: David H. Hollenberg, Neenah, Wis.

[73] Assignee: James River Corporation, Richmond, Va.

[21] Appl. No.: 635,378

[22] Filed: Jan. 2, 1991

Related U.S. Application Data

[63] Continuation of Ser. No. 372,477, Jun. 28, 1989, abandoned.

[51] Int. Cl.⁵ .................................. C08K 5/04
[52] U.S. Cl. ........................... 524/56; 524/58; 524/377; 524/386; 525/57; 525/61
[58] Field of Search ............ 524/377, 386, 56, 58; 525/61, 57

[56] References Cited

U.S. PATENT DOCUMENTS

| | | | |
|---|---|---|---|
| 3,767,784 | 10/1973 | Gluck | 424/18 |
| 3,963,685 | 6/1976 | Abrahams | 526/230 |
| 4,090,013 | 5/1978 | Ganslaw et al. | 526/15 |
| 4,410,571 | 10/1983 | Korpman | 427/385.5 |
| 4,552,938 | 11/1985 | Mikita et al. | 526/240 |
| 4,683,142 | 7/1987 | Zimmermann et al. | 427/2 |
| 4,693,713 | 9/1987 | Chmelir et al. | 604/368 |
| 4,737,582 | 4/1988 | Goldman et al. | 536/2 |

OTHER PUBLICATIONS

Behavior of Zirconium Compounds in Polymers—A Review, Warren B. Blumenthal, Polymer Engineering and Science, Nov. 1974, vo. 14, No. 11, pp. 754-759.

*Primary Examiner*—Paul R. Michl
*Assistant Examiner*—John Guarriello
*Attorney, Agent, or Firm*—Finnegan, Henderson, Farabow, Garrett & Dunner

[57] ABSTRACT

Metal ion crosslinked superabsorbent polymers and a process for making them are described wherein high concentrations of polyhydroxylated materials are incorporated in order to reduce the sensitivity of the superabsorbent composition to solutions containing dissolved salts. Also provided is a process for forming crosslinked superabsorbents containing high solids polymer content.

8 Claims, No Drawings

SUPERABSORBENT COMPOSITIONS AND A PROCESS FOR PREPARING THEM

This application is a continuation, of application Ser. No. 07/372.477, filed Jun. 28, 1989 now abandoned.

BACKGROUND OF THE INVENTION

The present invention relates to superabsorbent polymers and to a process for preparing them. More particularly, the invention relates to superabsorbent polymers having increased absorbency in the presence of dissolved salts. In addition, a new method for forming superabsorbents in a concentrated solution is disclosed.

Superabsorbents are generally composed of high molecular weight hydrophilic polymers that have been crosslinked to provide water-insoluble but water swellable materials. Depending on the type of polymer and the type and extent of crosslinking, these polymers may be capable of absorbing many times their own weight in fluid. Although a great variety of superabsorbents based on a wide range of chemistries have been described, there are basically just two methods for producing superabsorbents. One method involves polymerization of low molecular weight precursors to provide superabsorbents directly; the second method involves the crosslinking of preformed polymers. In forming superabsorbents by either method, the control of the amount of crosslinking (crosslink density) is very important with regard to the performance of the superabsorbent.

One of the problems associated with crosslinking of preformed polymers is that typically the polymer is of high molecular weight and when these materials are dissolved in water, they form very viscous solutions even at low concentrations. In order to thoroughly mix the crosslinker with the polymer, the solids in solution must be fairly dilute, on the order of 0.5% or less. Such extensive dilution requires large tankage capacity and the expenditure of much money, energy and time to rid the final polymer product of the water necessary to make it. Therefore, there is a need to develop a process wherein the polymer materials can be mixed at higher solids concentrations, thereby reducing the amount of water needed in the process and achieving savings in energy, size of equipment, effluent control and manufacturing time.

The present invention provides a method to form crosslinked superabsorbents at relatively high solids concentrations of polymer wherein low molecular weight, essentially non-ionic, hydrophilic molecules can be incorporated and immobilized. Incorporation of hydrophilic molecules, such as starches and saccharides in the composition, reduces both the cost of the superabsorbent as well as the sensitivity of the superabsorbent composition to dissolved salts in the aqueous medium. It also provides increased flexibility to the final composition. The superabsorbents thus produced may be used in thin film, powder, in a bulk form (thick film or plaque), or as a coating or binding for paper or non-wovens.

Additional objects and advantages of the invention will be set forth in the description which follows, and in part will be apparent from the description, or may be learned by practice of the invention. The objects and advantages of the invention may be realized and obtained by means of the instrumentalities and combinations particularly pointed out in the appended claims.

SUMMARY OF THE INVENTION

In the present invention, high concentrations of polymer solids can be incorporated into a superabsorbent composition by starting with an emulsion of a high molecular weight polymer, such as an alkali soluble polyelectrolyte, subsequently adding a suitable metal ion crosslinker to the bulk phase of the emulsion and then adding a volatile base to bring about in situ solubilization of the polymer. Subsequent evaporation of the water provides the superabsorbent. The advantage of this process is that the production of the superabsorbent is accomplished at a relatively high solids content.

Another advantage of the present invention is that it has been found that high concentrations of relatively low molecular weight polyhydroxylated compounds can be added to the mixture prior to solubilization. These materials are then incorporated into the final superabsorbent. Addition of these simple polyhydroxylated materials to the mixture results in superabsorbents with improved performance and provides a significant reduction in the cost of the superabsorbent on an absorbency per unit weight basis. The discovery that polyhydroxylated materials can be incorporated into the final crosslinked structure is not confined to the system where one uses an emulsion of the polyelectrolyte, but has been found useful in producing superabsorbents starting with solutions of polyhydroxylated materials admixed with solutions of polyelectrolytes as well as with emulsions of polyelectrolytes.

The types of polyhydroxylated materials that can be incorporated include, but are not limited to, simple diols and triols, simple mono-, di- and oligosaccharides, soluble starches, low molecular weight polyvinyl alcohols as well as other polyhydroxylated low molecular weight polymers. Admixture of these compounds with the polyelectrolytes should be done before the crosslinking via metal ions is accomplished. By use of the proper crosslinking ion(s), the polyhydroxylated materials will be immobilized in the final product. The mechanism by which these polyhydroxylated compounds are immobilized is not known. It could result from crosslinking of these materials with themselves as mediated by the metal ions, or they could be crosslinked with the polyelectrolyte via the metal ion, or they may react with the polyelectrolyte to form esters. Other mechanisms might also be responsible for immobilization.

While the use of metal ions as crosslinkers has been disclosed in the prior art, see for example U.S. Pat. No. 4,090,013, new modifications exist with regard to the applications of the present invention due to the relatively high solids content and/or the presence of polyhydroxylated materials. In dealing with emulsions, the metal ion must be stable to the pH of the bulk phase and should not react or interact with the ionic or organic dispersants or stabilizers. The amounts of crosslinker added will depend not only on the type of polyelectrolyte used but also on the type and amount of polyhydroxylated material used. Since the polyhydroxylated components are generally of lower molecular weight than the polyelectrolytes, as the proportion of polyhydroxylated material increases, the amount of added crosslinker must also increase. Although all of the metal ions previously disclosed in U.S. Pat. No. 4,090,013 may be used in the practice of the present invention, the use of zirconium ions alone or in admixture with ferric, aluminum, chromic, or titanium ions has been found to be especially useful.

These and other features and advantages of the present invention will be made more apparent from the following description of the preferred embodiment.

DETAILED DESCRIPTION OF THE PREFERRED EMBODIMENTS

A method is provided of preparing a superabsorbent composition that comprises (1) addition of a polyhydroxylate in a range up to 80% by weight to an alkali soluble polyelectrolyte in emulsion or solution, (2) adding a volatile neutralizing agent, if necessary, to adjust the pH of the solution to approximately 7, (3) adding metal crosslinkers having valences of three or more to the polyhydroxylate-polyelectrolyte emulsion and mixing thoroughly, and (4) drying the resultant mixture, i.e., in a convection oven, by microwave heating, by ambient evaporation or other conventional thermal processes.

In accordance with the preferred embodiment of the present invention, the superabsorbent of the present invention is composed of an emulsion of polyacrylic acid in water to which 50% to 80% saccharide in solution or in dry granules and a metal ion crosslinker containing zirconium are added and mixed. It is believed that the zirconium crosslinks the hydroxyl groups of the saccharide and ties it to the large crosslinked polymer thereby creating one large complexed molecule. The pH of the solution is neutralized, if necessary, by the addition of, e.g., ammonium hydroxide or ammonium carbonate or other volatile bases and the resultant mixture is dried. When starting with an emulsion of polyacrylic acid, the crosslinker can be added to the emulsion before pH adjustment.

The resultant films, plaques or foams, are then dried for use alone or added to a paper substrate and dried. These absorbent compositions can be used as films, foams or powders in absorbent products, binders or adhesives in non-wovens and composites, films or coatings in food wraps or multilayer laminants.

In the following examples, the polyelectrolytes are Acrysol A-3 or ASE-75, solutions and/or emulsions of polyacrylic acid in water, obtained from Rohm & Haas Company, Philadelphia, PA. The Zirtech crosslinkers, aluminum/zirconium lactate (AAL) and aluminum/zirconium acetate (LAA) were obtained from Zirtech, Inc., Gainesville, FL. The ammonium zirconium carbonate was obtained from Magnesium Elektron, Twickenham, U.K. Bacote 20 is a stabilized solution of zirconium ions available from Magnesium Elektron, Flemington, NJ.

The following examples demonstrate some of the many variations in compositions and procedures which can be followed.

EXAMPLE 1

A polyacrylate solution was prepared as follows: Acrysol A-3 (100 g solution, 25% solids) was mixed with solid sodium hydroxide pellets (8.2 g) to provide a solution of - 65% neutralized polyacrylic acid. Ammonium hydroxide (10.5 g, 28% $NH_3$ in water) and ammonium carbonate (5.0 g) were added to this solution and completely dissolved. Portions of this solution were also used in Examples 2-3 below.

A portion (10 g of solution, - 25% solids) of the Acrysol A-3 solution described above was mixed with maltose (3 grams). After the maltose dissolved in the polyacrylate solution, Bacote 20 (1.0 g of solution) was added. After thorough mixing, a portion of the material was dried in a microwave oven to a light, absorbent foam.

EXAMPLE 2

A portion (10 g of solution) of the Acrysol A-3 solution was mixed with a solution of glucose (5 g) dissolved in warm water (5 g). Bacote 20 (1.0 g of solution) was added, and after mixing a portion of this mixture was spread on a glass plate and allowed to dry at ambient temperature. After 24 hours, a thin flexible absorbent film was obtained.

EXAMPLE 3

A portion (10 g of solution) of the Acrysol A-3 solution was mixed with a solution of mannitol (3 g) in water (5 g). Bacote 20 (1.0 g solution) was added, and after mixing a portion of this solution was dried in a convection oven to provide an absorbent foam.

EXAMPLE 4

Acrysol ASE-75 (300 g, 120 g solids) was mixed with sucrose (120 g). This mixture was diluted to 2400 g with water. Aluminum/zirconium lactate (AAL) (9.3 g solution) was added, then ammonium hydroxide (29% ammonia in water) was added to bring the solution to pH of 7-7.5. The thick solution could be spread into films and dried at ambient conditions to provide an absorbent film.

EXAMPLE 5

Acrysol ASE-75 (1045 g, 418 g solids) was mixed with sucrose (324.5 g) and diluted to 3000 g with water. Aluminum/zirconium lactate (AAL) (112.3 g solution) was added and after thorough mixing, this suspension of latex and sugar was mixed with an equal volume of a saturated solution of ammonium carbonate. The resulting foam could be extruded into very thick films and dried in an oven at 105° C. to provide absorbent foams.

EXAMPLE 6

Acrysol ASE 75 (5 g, 2 g solids) was mixed with Aluminum/zirconium lactate (AAL) (0.6 g solution). Sucrose (1.0 g) was dissolved in water (0.5 ml), and this solution was added to the latex emulsion. A saturated solution of ammonium carbonate (5 ml, containing 2 drops of concentrated ammonium hydroxide) was added, and after stirring the mixture was dried in a microwave oven to a light foam.

EXAMPLE 7

Acrysol ASE-75 (5 g, 2 g solids) was mixed with a solution of sucrose (4 g) in water (8 g). Aluminum/zirconium lactate (AAL) (0.36 g) was added, and then a saturated solution of ammonium carbonate (10 ml, containing 0.5 ml concentrated ammonium hydroxide) was added with stirring. This material was dried in a microwave oven to a soft, absorbent foam.

EXAMPLE 8

Sucrose (15 g) was mixed with water (15 ml) and then added to ASE-75 (17 g, 22% solids solution). Aluminum/zirconium lactate (AAL) (3.5 g of solution) was added, and after thorough mixing, ammonium hydroxide was added (4 ml, 28% concentration), and the resulting thick solution was thoroughly mixed and spread in a thin film and dried in a convection oven to provide an absorbent, flexible film.

EXAMPLE 9

Sucrose (30 g) was dissolved in water (20 ml) and then added to ASE-75 emulsion (34 g of 22% solids solution). Aluminum/zirconium acetate (LAA) (7.3 g of solution) was added, and then just enough ammonium hydroxide was added to break the emulsion and form a gel. The gel was placed between two pieces of silicon-coated paper, flattened into a thick plaque, and dried in an oven for one and a half hours to provide a rigid plaque that becomes soft and flexible when exposed to high humidity.

EXAMPLE 10

Sucrose (10 g) was added to ASE-75 emulsion (25 g, 40% solids). Aluminum/zirconium acetate (LAA) (2.35 g of solution) was added, then solid ammonium carbonate (6.7 g) was added. The resulting foam was mixed and then dried in an oven for thirty minutes. The foam is stiff and brittle when removed from the oven but becomes soft and flexible when exposed to high humidity.

EXAMPLE 11

Sucrose (15 g) was mixed with ASE-75 emulsion (17 g, 22% solids). Ammonium zirconium carbonate (4.9 g of solution) was added. This induced the formation of a thick foam. The foam was placed on silicon-coated paper and dried in an oven.

What is claimed is:

1. A water-swellable, water-insoluble superabsorbent composition comprising an alkali-soluble polycarboxylated or polysulfonated polymer admixed with a polyhydroxylated material selected from a diol, a triol, a monosaccharide, a disaccharide, an oligosaccharide, a water-soluble polysaccharide and a low molecular weight water-soluble polyol, said admixture being crosslinked with a polyvalent metal ion crosslinker having a valence of at least 3 and neutralized by addition of a base to provide an absorbent polymer wherein the polyhydroxylated material is immobilized in said polymer.

2. A superabsorbent composition according to claim 1 wherein the metal ion crosslinker is a zirconium ion or a zirconium ion in admixture with a ferric, aluminum, chromic or titanium ion.

3. A superabsorbent composition according to claim 1 wherein the low molecular weight water-soluble polyol is polyvinyl alcohol.

4. A superabsorbent composition according to claim 1 which contains up to 90% by weight polycarboxylated or polysulfonated polymer.

5. A superabsorbent composition according to claim 1 wherein the alkali soluble polycarboxylated polymer is polyacrylic acid or a polyacrylate.

6. A superabsorbent composition according to claim 1 which contains from 10 to 80% by weight of polyhydroxylate.

7. A superabsorbent composition according to claim 1 which contains from 50 to 80% by weight of polyhydroxylate.

8. A superabsorbent composition according to claim 2 wherein the metal ion crosslinker is a zirconium ion admixed with an aluminum ion.

* * * * *